United States Patent [19]

Balassa

[11] Patent Number: 5,251,398
[45] Date of Patent: Oct. 12, 1993

[54] FIBROUS COATINGS FOR PROTECTING FRUIT BEARING OR BLOSSOMING TREES, SHRUBS OR OTHER VEGETATION FROM FREEZE AND FROST

[76] Inventor: Leslie L. Balassa, Shore Dr., Blooming Grove, N.Y. 10914

[21] Appl. No.: 557,924

[22] Filed: Jul. 25, 1990

Related U.S. Application Data

[60] Continuation-in-part of Ser. No. 518,726, May 4, 1990, which is a continuation-in-part of Ser. No. 259,174, Oct. 18, 1988, which is a continuation-in-part of Ser. No. 20,110, Apr. 24, 1987, Pat. No. 4,787,928, which is a division of Ser. No. 744,119, Jun. 12, 1985, Pat. No. 4,665,993.

[51] Int. Cl.$^5$ .............................................. A01G 13/00
[52] U.S. Cl. ................................................ 47/2; 47/58
[58] Field of Search .................................. 47/2, 9, 58

[56] References Cited

U.S. PATENT DOCUMENTS

| | | | |
|---|---|---|---|
| 2,875,555 | 3/1959 | Thiegs | 47/2 |
| 3,129,529 | 4/1964 | Rumsey | 47/2 CCB |
| 3,423,875 | 1/1969 | Bowker | 47/2 |
| 3,630,758 | 12/1971 | Despain | 47/2 |
| 3,790,395 | 2/1974 | Eron | 47/2 |

FOREIGN PATENT DOCUMENTS

224629 12/1984 Japan .................. 47/2 CCB

Primary Examiner—Henry E. Raduazo
Attorney, Agent, or Firm—Darby & Darby

[57] ABSTRACT

The present invention relates to a method of protecting vegetation from frost or freeze by providing a coating of a composition containing partially hydrated cellulosic fibers. The coating composition optionally includes an adhesive and/or a foaming surfactant. The method is particularly useful in protecting fruit-bearing and blossoming trees from frost or freeze. The present invention also relates to a composition of cellulosic fibers for use in the protective method.

18 Claims, 1 Drawing Sheet

FIBROUS COATINGS FOR PROTECTING FRUIT BEARING OR BLOSSOMING TREES, SHRUBS OR OTHER VEGETATION FROM FREEZE AND FROST

The present application is a continuation-in-part of pending U.S. application, Ser. No.: 518,726, filed May, 4, 1990; which is a continuation-in-part of pending U.S. application No. 259,174, filed Oct. 18 1988; which is a continuation-in-part of pending U.S. application, Ser. No.: 020,110, filed Apr. 24, 1987, now U.S. Pat. No.: 4,787,928, issued Nov. 29, 1988; which is a divisional of U.S. application, Ser. No.: 744,119, filed Jun. 12, 1985, now U.S. Pat. No.: 4,665,993, issued May 19, 1987.

FIELD OF THE INVENTION

The present invention relates to the preparation and use of a hydrated fibrous mass consisting of a slurry of cellulosic fibers swollen with water. More particularly, the present invention relates to the use of such a mass in firefighting, agricultural applications and in other applications where it is desirable to efficiently and economically apply large amounts of water to a large surface area without rapid dissipation or evaporation.

The present invention also relates to methods to aid in curing cement or concrete. More particularly, these methods relate to coating curing cement or concrete with a layer (or layers) of a protective, moist fibrous mass.

The present invention further relates to providing a covering of partially-hydrated fibers, optionally including an adhesive and a foaming surfactant, to protect trees, shrubs and other vegetation from frost or freeze.

BACKGROUND OF THE INVENTION

In firefighting, water has certain disadvantages which reduce its efficacy in extinguishing fires. The primary effect of water on fire is cooling, thereby reducing the ability of the fuel to burn, and displacement of oxygen necessary for the combustion of fuel. Unfortunately, water has a relatively high surface tension with attendant poor wetting properties for many surfaces. Water also has a low viscosity and flows well at any temperature between its freezing and boiling points. When water is brought into contact with very hot surfaces it has a tendency to bead and roll off the surface. This phenomenon is caused by the formation of a layer of steam between the hot surface and the water which acts to insulate the water from direct contact with the hot surface, reducing the ability of the water to absorb heat from the surface or displace oxygen.

Additives can be introduced to water used for firefighting to reduce the inherent disadvantages of water as a fire extinguishing agent. Surfactants can be added to water to improve its wetting properties. Gelling agents can be added to water to form a gel for use as a firefighting agent. Such gels, however, lose cohesion and viscosity on contact with hot surfaces. Foaming agents combined with water can be quite effective in smothering fires under special conditions. However, foams cannot be used in large fires since high winds created by major fires dissipate the foam or prevent its accurate application. In addition, in the case of chemical fires, burning chemicals frequently cause the collapse of the foam and consequent loss of most of its fire extinguishing properties.

Water retention is important in the curing of hydraulic cements, i.e., cements that are dependent on a hydration reaction for hardening, and concretes that are bound with hydraulic cements. The most common hydraulic cement for construction purposes is Portland cement, which is a heat-treated mixture primarily of calcium carbonate-rich material (such as limestone, marl or chalk) and material that is rich in $Al_2.SiO_2$ (such as clay or shale). Portland cement comes in several varieties which are distinguished by such characteristics as the rate at which they acquire strength during curing, the amount of heat of hydration that they generate, and their resistance to sulfate attack. Other types of hydraulic cements include aluminous cement, chalcedony cement (made from amorphous quartz) and Roman cement (made by mixing burnt clay or volcanic ash with lime and sand).

The term "concrete" describes to a mixture of stone, gravel or crushed rock and sand (the mixture termed "aggregate") which is bound by a cement. As used herein, the term "concrete" will include reinforced concrete (concrete that contains organic or silica-based fibers or metallic wire, cable or rods as a reinforcing substance) and polymer-cement concrete that is bound with Portland cement and a polymerized monomer or resin system. Hydraulic concrete and cement will be referred to henceforth as "cement". Additional information on the composition and characteristics of cement can be found in *Basic Construction Materials* (by C. A. Herubin and T. W. Narotta, third edition, Reston Book, Englewood, N.J.) which is incorporated herein by reference.

While the process of curing cement is water dependent, too much water interferes with the process. But, more importantly, too little water results in reduced strength. When cement is freshly poured, the water content may be higher than that which is optimal for proper curing. Thus, some water loss during the curing process can be useful. Often, however, the water loss during the curing process is too great and the cured cement has reduced strength. For instance, a graph on p. 186 of *Basic Construction Materials* (supra) compares the compressive strength after 180 days of concrete that was moist cured for 28 days vs. 14 days, 7 days, 3 days and 0 days. The results show decreases in compressive strength of approximately 8%, 21%, 32% and 55%, respectively (decreases interpolated from the graph). Excess drying during curing can also lead to the formation of surface cracks.

Consequently, a need to slow the rate of evaporative water loss from curing cement has long been recognized in the art. A previous method to control excessive drying of curing cement has been to apply water as a spray, mist or steam followed by covering the cement with a moisture barrier such as burlap, cotton mats, wet rugs, moist earth or sand, sawdust or other objects likely to act as a moisture barrier. Another method to control excessive drying during curing has been the application of a liquid membrane-forming composition, usually based on natural or synthetic waxes or resins and a volatile carrier solvent, to form, after volatilization of the carrier solvent, a moisture barrier that slows the rate of moisture loss from cement. Water-proof papers and plastic films have also been used.

The curing of cement and the quality of cement obtained is also dependent on temperature, with the recommended range between 55° and 90° F., and on other environmental factors such as wind and rain. In addition to ambient temperature, factors which influence the temperature of cement include the heat of hydration and heat from absorbed sunlight. Wind increases the drying rate of cement and can increase the rate of heat loss, while rain rehydrates cement and can potentially lower the temperature of cement. Of the prior art methods described above, the ones that best address at least one of these environmental factors are the liquid membrane-forming composition, the water-proof paper and the plastic film. These moisture barriers do not afford protection from solar energy or from cold weather.

Sudden frost or freeze is an almost annual occurrence in the temperate and in the semi-tropical zones. Frost or freeze, even of short duration can cause extensive loss of the blossoms and fruit in trees and shrubs. Blossoming trees and shrubs are particularly susceptible to freeze or frost damage. Freeze, if it is more than a few hours duration will damage or even kill fruit bearing trees. This is particularly the case with citrus trees. The "smudge pots" frequently resorted to protect fruit trees from frost or freeze are only marginally effective with frosts of short duration and are not at all effective in case of freeze. "Smudge pots" are also environmentally undesirable. Somewhat more effective in protecting the blossoms are continuous water spray mists or fogs. However, such water-sprays do not protect the trees themselves. Winding a protective tape on the trunk of the trees enables some trees to survive, but not their blossoms or even their leaves. Taping the tree is an expensive, labor intensive operation.

OBJECT OF THE INVENTION

It is an object of the present invention to provide a hydrated mat of fibers, capable of retaining large quantities of water for application to large surface areas where it is desirable to accurately direct large amounts of water economically and efficiently and to retain water on the surface area without rapid dissipation or evaporation.

It is a further object of the present invention to provide a dry mixture including substantially individual dry fibers which can be added to water for retaining large quantities of water after application to surface areas where it is desirable to accurately direct large amounts of water economically and efficiently and to retain water on the surface area without rapid dissipation or evaporation.

A still further object of the present invention to provide an inexpensive, efficient and environmentally sound method to control the rate of evaporative drying of curing cement.

Another object of this invention to provide a method of curing cement which provides thermal insulation for the curing cement, absorbs sunlight to warm the curing cement, reflects sunlight to protect the curing cement from excess heat, or provides a barrier against rain.

Still another object of the present invention is to provide a fibrous coating for vegetation, especially blossoming or fruit-bearing trees, which protects the vegetation from frost or freeze.

These and other objects of the present invention will be apparent to those of ordinary skill in the art in light of the present description and appended claims.

SUMMARY OF THE INVENTION

It has now been unexpectedly discovered that a hydrated mass of cellulosic fibers can be effectively used to extinguish fires and especially wood burning conflagrations. A hydrated fibrous mass can also be used as a carrier for pesticides, as a concrete or cement cure rate controlling agent, and as a dust suppressive agent.

The hydrated mass is prepared by the steps including introducing a source of cellulosic fibers to water with continuous mixing until a ratio of water to fibers of about 50 to 1 is obtained, and mixing the water and source of cellulosic fibers until the source of cellulosic fibers has been comminuted to substantially individual cellulose fibers.

In another embodiment of the invention, the rate of evaporative drying of curing cement can be controlled by overlaying the curing cement with at least one layer of such a hydrated mass composed of cellulose fibers, a viscosity enhancing polymer, a hygroscopic swelling agent and, optionally, an adhesion reducing agent.

In still another embodiment, the invention provides further protection of curing cement against wind, rain, and cold or warm weather by selection of appropriate additives to said hydrated mass and, optionally, stacking layers of such hydrated mass (for instance, to sandwich a layer of an insulative cellulosic composition between two layers of the basic composition).

It has also been discovered that a number of short staple fibers together with suitable adjuvants are capable of forming a tent-like protective cover for trees and shrubs and an insulating coat for the blossoms.

DESCRIPTION OF THE INVENTION

One object of the invention is met by providing a hydrated mass of fibers comprising water retained in a carrier of cellulosic fibers. It is well-known that cellulose fibers absorb up to 20 times their weight in water and a mass of such fibers is capable of retaining additional water immobilized by adsorption. A fibrous mat formed from a mass of cellulose fibers and water forms an inexpensive, non-flowing wet blanket.

Depending on the desired application, the characteristics of the fibrous mass can be determined by the type of cellulose fibers selected, the length of the fibers used, the pH of the water retained by the fibrous mass, and by chemical additives to the water which can enhance various characteristics of the hydrated fibrous mass.

Figure 1:
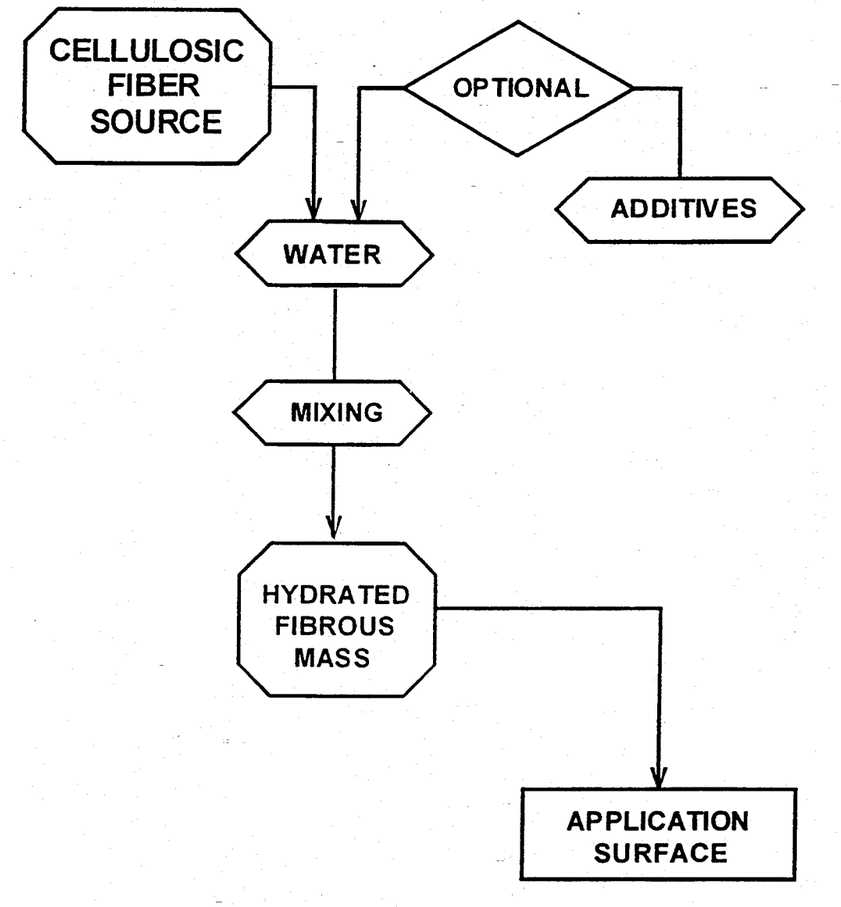
FIG. 1 shows a flow diagram of the method of the present invention, including the steps for preparing the hydrated fibrous mass, and the application of the mass to a surface.

Any cellulosic fiber can be used as the carrier to form the fibrous mass provided that the material is capable of being shredded, beaten or pulped into fibers which are capable of swelling in water and forming a fibrous mat. Preferred fiber length is from 2 to 10 mm. Shredded newsprint is the preferred source of cellulosic fibers. Newsprint is readily available in virtually unlimited quantities at low cost and is bio-degradable and therefore ecologically acceptable for use in fighting brush or grass fires for example, or for use in agricultural or construction applications. Other types of materials from which cellulosic fibers can be obtained include wood pulp, shredded corn cob, straw, leaves and other types of cellulosic bio-mass. Well-known chemical additives can be introduced to water used in forming the mass to assist in causing swelling of the cellulosic fibers. Urea, sodium hydroxide and potassium hydroxide are examples of such additives. Swelling is a function of the capacity of the fiber to absorb water, but not all absorbing fibers will swell and retain water. Non-absorbing fibers do not retain water except for retention due to adsorption. FIG. 1 shows a flow diagram of one method of the present invention, including the steps for preparing the hydrated fibrous mass and application of the mass to an application surface.

The object of controlling the rate of drying of curing cement is met by providing a moisture barrier in the form of such a hydrated mass of fibers. The drying rate of this hydrated mass is quite slow. The rate can be slowed further by the addition of a hygroscopic swelling agent and a viscosity enhancing polymer. The viscosity enhancing polymer also functions to assist in dispersing the cellulose during preparation or dilution of the cellulosic mass. The viscosity enhancing polymer further functions to increase the viscosity of the cellulosic mass, thereby increasing the cohesiveness of the material. Examples of the viscosity enhancing polymers useful as additives to the hydrated mass include cellulose derivatives, marine-derived gums such as Carrageenan, polyvinyl alcohols, methylcellulose, ethylcellulose, methyl-propylcellulose, carboxymethylcellulose, and acetates of polyvinyl alcohols. Examples of hygroscopic swelling agents useful as additives in the invention are urea, guanidinium hydrochloride, glycerol, glycerol mono- and di-stearate, other mono- and diacyl ($C_9$ to $C_{28}$) glycerides, phosphoric acid, and ethylene glycol.

The hydrated mass has a tendency to adhere tenaciously to cement at the completion of the curing process. This adherence can make removal of the cellulosic composition labor intensive. However, this problem can be overcome by the addition of an adhesion reducing compound. One class of such adhesion reducing compounds includes acidic lipids and their salts. Examples of such acidic lipids are fatty acids, and lower alkyl sulfates or sulfonates. Preferred fatty acid and alkyl chain lengths are 9 to 28 carbons. Particularly preferred as an adhesion reducing compound is ammonium stearate. Examples of salts useful as adhesion reducing compounds are the sodium, potassium, ($C_1$ to $C_6$) alkyl ammonium, and ammonium salts of the above described fatty acids and alkyl sulfates and sulfonates.

The use in the invention of acidic lipid salts wherein the positive ions are basic compounds which can volatilize in the uncharged form, leaving the hydrophobic free acid, provides a further advantage. Soon after application of such cellulosic coverings, the cations located on the outer-most surface tend to volatilize, leaving a uniform dispersion of water-immiscible compounds that provide a barrier against rain. This water-immiscible barrier also blocks the wicking action of the cellulose fibers that can accelerate the drying of the cellulosic mass. Examples of such volatile cations are the $C_1$ to $C_6$ alkyl ammonium ions and the ammonium ions. The ammonium ion is preferred. Among the corresponding fatty acid salts, ammonium stearate is particularly preferred.

Other adhesion lowering substances may be used, alone or in combination with fatty acids. These include talc, mica, pyrophillite, montmorillonite, vermiculite, pearlite, aluminum flakes, and graphite. Among these, aluminum flakes, talc and mica are preferred. Aluminum flakes are less preferred only because of their high cost and their reactivity.

For this cement curing embodiment, the preferred processed cellulose fiber length is 0.2 to 5 mm.

Other cement curing embodiments of the invention can be prepared by adding an appropriate additive to the cellulosic composition and by using multiple layers. For instance, as mentioned above, the outer surface of cellulosic mass covering the cement can be made water resistant by the addition of an acidic lipid combined with a volatile basic compound such as ammonia. The surface may also be made reflective of sunlight by the addition of reflective additives such as titanium dioxide, silica, lithopone, zinc oxide, and bleached paper pulp. Conversely, the surface may be made more light absorptive by addition of pigments such as carbon black, lamp black, and black iron oxide. The cellulosic mass can be made more heat insulative by addition of a heat insulative material such as vermiculite, fiber glass, asbestos, resin-coated cellulose, polyethylene coated cardboard, volcanic ash, mica and ground corncobs or peanut shells.

In a preferred cement curing embodiment, an insulating layer is sandwiched between two other cellulosic layers. One may combine the above described embodiments. For instance, one might cover cement with three layers wherein the outermost is reflective and water-resistant, the middle layer is insulative, and the cement-contacting layer is the basic cellulosic composition.

Preferred component ranges for the cement curing compositions are given below by percent of total minus water:

|  | Preferred | More Preferred |
| --- | --- | --- |
| Fiber | 20–80 | 40–60 |
| Viscosity Enhancing Polymer | 2–30 | 6–10 |
| Hygroscopic Swelling Agent | 5–40 | 15–30 |
| Adhesion Reducing Compound | 10–40 | 15–30 |
| Solar Reflective Agent | 5–20 | 5–10 |
| Solar Absorptive Agent | 3–20 | 3–8 |
| Insulative Agent | 20–50 | 20–30 |

Water may be added to the initial composition as a mixing aid, e.g., 30–90% of the initial composition. Additional water is then added in amounts depending on the method of application to be used. This can vary with several factors. If the composition is to be applied by spraying, the dilution varies with the type of spray nozzle, the pressure obtained from the pump, the distance the composition must be thrown, etc. If applied by brushing, dilution can vary with the type of brush, the viscosity of the composition, the surface tension of the composition, etc. Generally, the dilution will be between about 10 to 20 fold. The final weight water to weight fiber ratio will be between 1 and 99, preferably between about 15 and about 70.

Another embodiment of the invention uses a non-cellulosic top layer over one or more of the cellulosic layers. This top layer is composed of aluminum flakes and a film-forming polymer, such as ethyl cellulose, cellulose acetate, modified starch, and polyvinyl alcohol, and applied as a dispersion in water or in a volatile carrier solvent such as ethylacetate, low boiling hydrocarbons, benzene or halogenated hydrocarbons.

The present invention also provides a coating of partially hydrated cellulose fibers with considerable thermal insulation capability. When suitably applied, this coating will protect the trees and shrubs together with their blossoms and leaves against frost and freeze of relatively short duration. The fiber composition may contain surfactants and adhesives to enhance their adhesion the fruits and vegetables to be protected. The fiber composition may also be used as a carrier for pesticides and antifreeze chemicals which retard the freezing. The fiber composition may be used in combination with foams to protect particularly tender blossoms against mechanical damage during subsequent clean up to remove the fiber composition.

The semi-hydrated fiber composition is prepared from paper or cardboard ground in a hammer mill or any other type of mill for grinding paper or cardboard. Water may be added to the fiber source (e.g. paper or cardboard) to facilitate the grinding process. Preferably, between about 15% and about 20% water (v/wt of fiber source) is added for this purpose. Other materials from which suitable fibers can be obtained include wood pulp, shredded corn cob, straw, leaves and other types of cellulosic biomass.

Preferrably, a coating having a thickness between about 4 cm and about 12 cm is applied to the trunks of trees, more preferrably between about 8 cm and about 12 cm. The coating thickness for blossoms and foliage is preferrably between about 0.5 cm and about 5 cm.

As in other embodiments of the present application, polymer coated paper or cardboard may be used as the source of cellulosic fibers (e.g. polyethylene-coated). Polyethylene-coated paper usually contains between about 5 and about 20% polyethylene by weight, most often about 10%. Thermal insulation compositions made with this paper retain (and require) less water.

In general, if colder weather is anticipated it is preferable to have less water in the insulative composition. This is because water present in the composition can potentially lead to evaporative cooling.

The ground fibers are applied to the plants in the orchards by spraying them through a pneumatic tube (e.g., Hagan Insulative Equipment, Hagan Manufacturing, Delphos, Ohio) such as those employed in the cellulose fiber insulation industry. The fibers ejected from the tube are partially hydrated by a mist of water from one or more water jets aimed on the path of the ejected fibers. The hydrating spray will, preferably, contain sufficient water-soluble adhesive to cement the fibers to the trees, blossoms, fruits and vegetables.

The hydrating solution to fiber weight ratio is preferably between about 5:60 and about 20:60, most preferably between about 8:60 and about 14:60. The amount of watersoluble adhesive is between about 1% and about 20% w/v, more preferably between about 2% and about 5% w/v.

To protect sensitive blossoms from mechanical damage during the removal of the fiber coating after the danger of freeze has passed, a coating of water-soluble foam may be applied prior to or in combination with application of the fiber composition. The foam may be applied by numerous spraying devices, including the water jets and the pneumatic tube described above.

The foaming surfactant may be included in the hydration solution. If so, the amount is preferably between about 2% and about 5% w/v. If the surfactant is applied to the vegetation prior to application of the fiber composition, preferably an aqueous solution containing between about 2% and about 10% w/v is applied. More preferably, a solution having between about 2% and about 5% w/v is applied.

A particularly preferred surfactant is Aerosol 18 TM (Disodium N-octadecyl sulfosuccinamide), supplied by the American Cyanamid Co. (Wayne, N.J.). Other members of this family of surfactants may also be used, e.g.:

Where M is sodium or potassium.
Where $R_1$ is H, carboxy $C_{2-4}$)alkyl or its sodium or potassium salts, or dicarboxy($C_{2-4}$) alkyl or its sodium or potassium salts.
Where $R_2$ is ($C_{14-22}$)alkyl.
And where $R_3$ and $R_4$ are $C_{(8-12)}$ alkyl.

Aerosol 18 is formula I where $R_1$ is H and $R_2$ is octadecyl. Also preferred is Aerosol 22 TM (American Cyanamid) which is formula I where $R_1$ is 1,2-dicarboxyethyl and $R_2$ is octadecyl and Aerosol OT TM (American Cyanimid) which is formula II where $R_3$ and $R_4$ are 2-ethylhexyl. Other surfactants, such as salts of the ($C_{14-22}$)alkyl sulfates (e.g. sodium dodecylsulfate), salts of various arylalkylsulfonates (and hydroxylated analogs), etc. may also be used.

In the application of the fiber composition or the foam coat, the pneumatic tube may be replaced by a modified Reinco "Power Mulcher", made by Reinco, Plainfield, NJ. This machine has the capacity to throw these materials high enough to reach the top of the trees.

Among the antifreeze chemicals which may be added to the fiber composition are various antifreeze proteins and peptides obtained from fish and eels (see Cutler et al., *J. Plant Physiol.* 135:351-354, 1989; Ananthanarayanan, *Life Chem. Rep.* 7:1-32, 1989; Cheng et al., *Biochem. Biophys. Acta* 997:55-64, 1989; and Chakrabatty et al., *J. Biol. Chem.* 264:11313-11316, 1989). Ice nucleation-deficient bacteria may also be added as frost protection agents (see Warren et al., *ACS Symposium Series*, Vol. 334, pp. 215-227). (All patents and publications disclosed in this application are incorporated herein by reference.)

The present invention is described further by the following non-limiting examples.

EXAMPLE 1

A hydrated fibrous mass for use in firefighting was prepared by introducing 1,000 ml (milliliters) of water having a pH of 6 to a Vita Mix Model 3600 mixer from Vita-Mix Corp., Cleveland, Ohio. 55 grams of shredded newsprint having 5% moisture content were introduced to the mixer while the mixer was running at low speed (150 rpm)(revolutions per minute). The newsprint was gradually introduced over a period of 5 minutes. After all of the newsprint had been added to the mixer, the speed of the mixer was increased to about 3,000 rpm. After five minutes of mixing at 3,000 rpm, a homogeneous non-flowing mass was obtained. The viscosity of the mass was determined to be approximately 500 cps (centipoise). On horizontal surfaces the hydrated fibrous mat can be built up to a thickness of 4 to 6 centimeters. On vertical surfaces, the mat can be applied in thicknesses of up to 0.5 to 1.0 centimeters.

Providing water with an alkaline pH aids in disintegrating the newsprint into individual cellulose fibers.

The hydrated fibrous mass of Example 1 can be used to quickly extinguish brush or grass fires, as well as industrial or structure fires, by blanketing the area affected with the hydrated fibrous mass to form a fibrous mat on the ground. Due to the density and rheology of the fibrous mass, the mass will remain in contact even with inclined surfaces (such as burning trees). The fibrous mass can also be used to prevent the spreading of a fire by covering forest floor litter and brush.

A low pH is not preferred unless a swelling agent such as phosphoric acid ($H_3PO_4$) is required.

The hydrated fibrous mass of the present invention should not be used to extinguish fires where water is contraindicated. Such fires include crude oil, gasoline, electricity and machinery fires as well as certain types of chemical fires.

The fibrous mass can be prepared ahead of time and then transported to the scene of a fire. The mass can be stored in containers of convenient size and weight. Paper or plastic bags of 25 to 100 pound capacity are acceptable. The prepared mass can then be transported by air to the scene of a fire and then ejected from a plane or other aircraft onto the fire. Alternatively, the mass can be prepared from separate water and fibers on board an aircraft, for example, and then ejected onto a fire. The prepared mass may also be transported by tank truck equipped with a pumper/mixer such as a Finn Hydroseeder, or similar device. Depending on fiber content, the mass can be applied by spraying through nozzles (fiber content of 2–5%), thrown by rotating throw wheels or dropped from the air by plane or other aircraft (fiber content of 5–10%).

EXAMPLE 2 (firefighting)

A hydrated fibrous mass of low mobility and high rheological resistance was prepared by introducing 1,000 liters of tap water at pH 5.5 to a Cowles-type disperser (obtained from Myers Engineering, Bell, California) having a 30 centimeter blade, a 20 horsepower motor, and a capacity of 1,000 liters. The water was introduced to the disperser and the mixer was operated at 200 rpm. 100 kilograms of shredded newsprint having a 5% moisture content were added to the mixer as in Example 1, with the disperser mixing at approximately 200 rpm. After the introduction of the newsprint, the speed of the disperser was increased to approximately 750–1,000 rpm and mixing continued until a homogeneous dispersion was obtained (after approximately 15 minutes).

The material obtained is non-flowing, having a viscosity of approximately 1,000 cps, and may be built up to about 10 centimeters thickness on a horizontal surface. A hydrated mass of this viscosity is of particular value in protecting buildings in city fires, for example, by blanketing the roof of a building adjacent to a burning building, thereby preventing sparks and cinders being emitted from the burning building from igniting the fiber-procted building.

In certain applications it is desirable to provide the hydrated mass with additives which act as fire retarding agents. For example, in large-scale fires wherein high temperatures in excess of 1500° F. are encountered for more than one hour, the hydrated mass may be heated for such a duration that the retained water is evaporated, leaving dried cellulose fibers. To prevent these fibers from becoming fuel for the fire sought to be extinguished, fire retardant agents can be employed as adjuvants. These agents may be dissolved in the water introduced to the mixer prior to the addition of shredded newsprint or other sources of cellulosic fibers. Fire retardant agents which may be used include the following:

| Compound | Effective Range | Preferred Range |
|---|---|---|
| Tri-sodium phosphate | 1–10* | 3 |
| Tri-potassium phosphate | 1–10 | 3 |
| Diammonium phosphate | 10–300 | 100 |
| Di-potassium phosphate | 10–300 | 100 |
| Borax** | 1–100 | 30 |
| Urea | 1–100 | 50 |
| Sodium Silicate | 1–100 | 50 |
| Ammonium Sulfate | 1–100 | 50 |

*Units are % of dry fiber weight.
**Borates such as Borax are not to be used when vegetation is to grow on the site following the fire.

These agents act to prevent the dried fibers from becoming a fuel source by absorbing or adsorbing onto the fiber and causing the fiber to char without flame and without forming glowing embers.

It is important that the cellulose source be broken down as closely to single fiber structure as possible so that the total water absorbing surface area of each fiber is maximized. By using substantially individual fibers, the water adhesion benefits of cohesion caused by adjacent individual fibers can be effectively harnessed in providing an effective water-holding mat. Although water is used in the above described first embodiment in order to break down the cellulose source into its basic fibrous structure, the individual fibers may also be created without the use of water, as further described in a second embodiment below.

The cellulose fibers may be prepared directly from the cellulose source through dry milling or grinding processes, e.g., hammer milling, roller milling, ball milling or any other impact or attrition processes which result in the breaking down of the cellulose source substantially to its basic fibrous structure without the addition of water.

The preferred process is to grind the cellulose source, e.g., newsprint or cardboard box material in a hammer mill equipped with flat-edged hammer blades and a suitable screen to control the particle size of the ground product. In order to prevent dust explosion during grinding or immediately following grinding, the air in the mill may be replaced with an inert gas, e.g., nitrogen or carbon dioxide. If straw or corn husks or any other siliceous cellulose source is to be ground, the grinding should be preferably done in an atmosphere of dry steam.

The substantially individual dry cellulose fibers as prepared above, may be mixed either during grinding or following grinding, with various additives such as surfactants, dyes, plant nutrients, herbicides or fire suppressants. The fibers with or without the additives may be dispersed in water for application via suitable conventional spray equipment. A particularly suitable method of applying the dry fibers with or without the additives is by blowing them through a tube with air pressure, supplied by a pump or by compressed air, and forcing the material into the center of a cone of swirling high-pressure water moving at high velocity in the same direction. In this manner, a swirling stream of wet fibers is created, and may be sprayed on the ground or on vegetation at a thickness more easily controlled than if the material was predispersed in the water.

The fiber dispersions may then be applied to steep hills or even to vertical walls without danger of being blown off by even strong winds or washed off by hard rains.

In order to illustrate the second embodiment of the present invention, reference is made to the following examples which are not intended to limit the invention in any respect.

EXAMPLE 3

Newsprint was ground in a Model D-6 Fitz Mill, a hammer mill, supplied by The Fitzpatrick Co. of Elmhurst, Ill. This mill has 16 impact type hammers operating in a 6 inch wide chamber at about 7,200 rpm and a screen area of 109 square inches having perforations of 0.25 inch diameter circular openings.

A single pass through the screen resulted in comminuted fibrous particles having a range of particle sizes between about 0.01 and 0.25 inches. By passing through the screen twice or three times the paper was ground to a more uniform pulp with particles primarily in the smaller size ranges of 0.01 and 0.03 inches (alternately, screens with successively finer openings may be employed).

EXAMPLE 4

Corrugated cardboard was ground with a Model D-6 Fitz Mill at 7,200 rpm through screen perforations of 0.30 inch diameter circular openings. One pass resulted in a particle size range of 0.05 and 0.1 inch diameters.

EXAMPLE 5

Wheat straw was ground with a Model DK-6 Fitz Mill equipped with 16 Code 225 fixed blades having a knife edge on one side and an impact edge on the other and with means for the introduction of steam or inert gases such as nitrogen or CO2. The screen used had perforations of 0.6 inch diameter. The processing was done in a dry steam atmosphere to prevent self-ignition of the straw. By operating the mill at about 9000 rpm and using the knife edge of the blades a product was obtained with a particle size range of 0.2 to 0.5 inches in a single pass through. By operating the mill at about 6,000 rpm the particle size of the product was shifted to be nearer the 0.5 inch range.

EXAMPLE 6

Newsprint paper was moistened and compacted by passing multiple sheets between heated steel rollers under sufficient pressure to effect the compacting. The compacted material was shredded with a cross cutting shredder and then ball milled in a steel mill with steel balls of 1 to 3 inch diameter as the grinding medium. The mill was flooded with CO2 to prevent a dust explosion during grinding. The grinding was done with the mill loaded 30% of its volume with the balls and up to 60% with the shredded material. The grinding was completed when the material was reduced to the desired particle size. The grinding step took from about 6 to 24 hours.

EXAMPLE 7

Fire retardant composition was prepared in the following manner. A cylindrical mixing tank of 100 gallons gross capacity and equipped with a 5 horse power closed turbine mixer made by the Arde Barinco Corp. of Mahwah, N.J. was found to be suitable mixing equipment. 154.5 kg (40 gal.) of tapwater of ambient temperature was introduced into the tank. The mixer was activated and the speed set for 3600 rpm. The fire retardant ingredients were introduced into the tank in the order listed:

| | |
|---|---|
| Carboxymethyl cellulose, low viscosity grade, sodium salt | 1.1 kg |
| Methylcellulose, 4000 cps grade | 0.5 kg |
| Diammonium phosphate | 2.2 kg |
| paper pulp of Example 3 | 2.2 kg |
| Total solids | 6.0 kg |

In field tests on wood pallets this composition was found to be 15 to 20 times as effective as water in suppressing fire under comparable conditions. Carboxymethyl cellulose, potassium salt, may be substituted for the sodium salt, for increased efficacy.

EXAMPLE 8

A cement curing composition was prepared utilizing the same mixing equipment as described in Example 7. The composition was prepared by mixing the following ingredients:

| | |
|---|---|
| Tap water | 150.0 kg |
| Carboxymethyl cellulose, sodium salt | 1.0 kg |
| Sodium lignosulphonate | 0.5 kg |
| Paper pulp of Example 3 | 5.0 kg |
| Total solids | 6.5 kg |

This composition was sprayed on a cement road surface (which had been laid six hours previously) with a wet thickness of about one inch. The cement cured well and had to be remoistened only once in three days. An untreated cement surface dries in a short time but with undesirable mechanical properties. Known methods to prevent this effect involve laying wet burlap or cotton sheeting on the cement surface. The burlap or cotton sheeting require frequent wetting and frequently results in mold formation under the burlap or cotton sheeting or the cement surface. In addition, the burlap or cotton sheeting are difficult to apply to steeply inclined or to vertical surfaces.

EXAMPLE 9

A composition for curing cement on inclined or vertical structures was prepared using the mixing equipment of Example 7. The composition was prepared by mixing the following ingredients:

| | |
|---|---|
| Tap-water | 200.0 kg |
| Carboxymethyl cellulose, sodium salt | 1.0 kg |
| Glyceryl monostearate | 2.0 kg |

The carboxymethyl cellulose and the glyceryl monostearate added to the water with the mixer operating at full speed (from 360 to 9000 rpm). The glyceryl monostearate acts to reduce the tendency of the paper fibers to adhere to the cement surface.

Using a tube and high pressure air (as described in the description of the second embodiment of the present invention), the dry fiber pulp of Example 3 was blown into a cone shape formed by the above solution moving in a swirling fashion at a high velocity, under high pressure, at a ratio of 1 to 5, fiber pulp to water. The material could be built up to more than one inch on inclined or vertical surfaces. The cement cured well after re-wetting the surface only twice.

EXAMPLE 10

A composition was prepared for the prevention of freezing of moisture found in ores, coal, etc. stored outside or transported in open freight cars during below freezing temperatures.

The equipment used was Model T 50 Hydroseeder of the Finn Corp. of Ohio, with a mixing tank of 500 gallon working capacity. Mixing of the composition was accomplished through dual action paddle agitation combined with recirculation.

| | |
|---|---|
| Tap-water | 400.0 gal. |
| Paper pulp of Example 3 | 64.0 lb |
| Urea | 64.0 lb |

This material protected coal piles outdoors in severe cold weather from freezing. The material was sprayed on coal lumps, as piles of coal were being formed. In addition, the material was sprayed to create a blanket on the coal pile. This treatment prevented the coal in the pile from freezing to a solid mass.

EXAMPLE 11

Laying of dust and suppression of flying dust in mines and quarries was accomplished with the following composition. The equipment used was the same as in Example 10. The following ingredients were mixed:

| | |
|---|---|
| Tap-water | 400.0 gal. |
| Paper pulp of Example 3 | 64.0 lb |
| Sodium lignosulphonate | 6.4 lb |
| Urea | 12.8 lb |

The composition was sprayed on surfaces which were exposed to dust and to equipment generating dust. The dust was kept down by this treatment and flying dust was reduced by about 95%.

EXAMPLE 12

Spray-sod for lawns was prepared using the application equipment described in Example 9. Lawns were prepared as follows.

The soil was fine graded, fertilized and seeded. The paper pulp of Example 3 was applied evenly in a thickness of about ¼ inch. The grass came through the fibrous mat within three days. The seeds on the control plot which had no fibrous mat covering, sprouted four days later. Throughout the following four months the plot with the hydrous mat showed much better and denser growth than the control. The grass roots under the fibrous mat were also developed more than twice as well as on the control plot.

EXAMPLE 13

Spray-sod for lawns during planting of seeds in late fall at the onset of cold weather or during drought conditions when the lack of moisture retards or prevents the sprouting of the seeds requires a fibrous covering in excess of ¼ inch thickness. The most desirable fibrous mat thickness under these conditions is in the range of 1 to 3 inches. However, paper pulp of the type of Example 3, tend to form a tight "papier mache" film which would actually retard the sprouting of the seeds, retard or completely prevent the breaking through of the grass. Also the impervious papier mache mat is conducive to mold growth on the side close to the ground. Mold is destructive to seeds and sprouts. None of these difficulties are found with straw mulches, which allow air to circulate through the mulch. However, straw has a very low water holding capacity and does not form a suitable mat if used by itself. Therefore, ground straw in combination with the paper pulp was used as follows. Mat Compositions:

| | |
|---|---|
| a) Paper pulp Example 3 | 75% |
| Wheat straw Example 5 (6000 rpm grind) | 25% |
| b) Paper pulp Example 3 | 50% |
| Wheat straw Example 5 (6000 rpm grind) | 50% |
| c) Paper pulp Example 3 | 25% |
| Wheat straw Example 5 | 75% |

Results: Cohesion of the mat: a) Excellent, only slightly less than straight pulp; b) substantially less than a); c) much less cohesion than even b) but still holding together.

Oat hulls, wheat chaff, or rice straw, or other cereal straw, may be substituted for wheat straw in the above compositions.

To test the ability of the wet pulp to adhere to dry pine boards when sprayed layers of about one inch thickness were formed. The boards were set at an angle of seventy degrees: Paper pulp control excellent a) equal to control; b) weaker adhesion than control, tends to slide off; c) shows poor adhesion, strong tendency to slide off the board.

Conclusion: Paper pulp of Example 3 combined with wheat straw of Example 5 up to a weight ratio of 50:50 forms a suitable mulch for application in thickness of greater than ½ inch either to level or even to steeply inclined surfaces, e.g., embankments. It should be noted that straw, although used generally as a mulch, is not satisfactory because wind blows it away even from flat ground and even more so from inclined ground, necessitating the use of plastic netting or an adhesive to prevent the straw from being blown away.

The cardboard pulp Example 4 may be used as a replacement for paper pulp of Example 3 in Examples 8, 9, 10, 11 and 12. It may also be used in combination with straw, however, the adhesion of the mulch to inclined surfaces will be lower than is the case with Example 3. Cardboard mulch does not form the tough papier mache film as readily as the paper mulch formed with Example 3 or Example 6. At similar particle size distribution, no significant difference between the hammer mill ground material of Example 3 and the ball mill ground material of Example 6 was found.

EXAMPLE 14

The following materials were mixed to form a cellulosic mass use in cement curing:

| Component | % by weight |
|---|---|
| Water (tap-water at room temperature) | 91.0 |
| Ground newsprint (hammer-milled, average fiber length was 2 mm) | 4.5 |
| Urea (fertilizer grade, pulverized, City Chemical Co., NY) | 2.5 |
| Carrageenan (Gelcarin XP7013, FMC Corp., NY, NY) | 2.0 |

The water was introduced into a container equipped with a homogenizing mixer and the mixer was activated to about 1500 rpm. The ground newsprint, urea and Carrageenan were introduced incrementally and in this order. After all components were added, the speed of the mixer was increased to about 3000 rpm and mixing was continued until a homogeneous mix was obtained (about 5 minutes).

This cement curing composition was tested and found to pass the standard set by the American Society of Testing and Materials (ASTM) under specification C309. With an application of this composition of 15 ft$^2$/gal, the underlying cement showed a loss of water of only 0.54 kg/m$^2$ over a period of 72 hours. The composition was applied with a one inch soft brush. Upon completion of this test, a residue of this composition was found to adhere tenaciously to the cement substrate requiring warm water and scouring with a stiff brush to strip it from the surface of the cement.

EXAMPLE 15

The following materials were mixed to form a cellulosic mass with a water resistant surface and reduced adherence to cement:

| Component | Amount |
| --- | --- |
| Stearic acid, USP fine granules | 50.0 g |
| Water, 70° C. | 500.0 g |
| Ammonia, technical, quantity sufficient to neutralize the stearic acid (City Chemical Co., NY) | q.s.* |
| Urea | 20.0 g |
| Carboxymethylcellulose (Aqualon Co., Wilmington, DE) | 10.0 g |
| Ground newsprint, 120 to 150 micron fibers | 50.0 g |
| Additional water depending on the method of application | q.s. |

*Quantity sufficient.

The stearic acid and water were placed in a jacketed mixing vessel equipped with a turbine mixer. The vessel was then brought to a temperature of about 80° C and the mixer activated to a speed of about 1500 rpm. Sufficient ammonia was added to bring the pH to between 7.0 and 7.5 (approximately 3 g) and the vessel temperature reduced to 20° C. The mixer speed was increased to 4000 rpm. Urea and carboxymethylcellulose were added incrementally so as to prevent the agglomeration of the carboxymethylcellulose. Next, the ground newsprint was added. Finally, additional water was added to give the consistency appropriate for the mode of application (approximately, a 10 to 20 fold dilution). The mixing was continued until a homogeneous dispersion resulted.

This cement curing composition showed a loss of water from the underlying cement of 0.53 kg/m$^2$ when subjected to the ASTM C309 test. After curing, this composition was completely removed from the substrate using rotating scrub brushes. No stain was left on the cured cement surface.

This ammonium stearate-containing composition acquires a water-resistant surface soon after it was applied. This water-resistant surface should reduce the wicking action that can accelerate the drying of the cellulosic mass.

Other long-chain fatty acids, such as palmitic, myristic, iso-stearic and oleic acid, may be used in place of stearic acid to give cellulosic compositions with reduced adherence to cement.

EXAMPLE 16a

The following formulation was used to make another cellulosic mass with reduced adherence to cement:

| Component | Amount |
| --- | --- |
| Mica, flakes ground to 1 to 5 mm (English Mica Co., King's Mt., NC) | 45.0 g |
| Sodium lauryl-sulfate (Dupont, Wilmington, DE) | 2.0 g |
| Urea | 20.0 g |
| Carboxymethylcellulose | 5.0 g |
| Ground newsprint, fiber length 150 to 200 microns | 45.0 g |
| Water at room temperature | 600.0 g |

The mica, sodium lauryl-sulfate, urea, carboxymethylcellulose and newsprint were dry mixed in a Hobart Kitchen-Aid Mixer (Model K4-B, Hobart Manufacturing, Inc., Tory, Ohio) and, while the mixing continued, 600 g of water were added as a fine spray. Approximately 2000 g of additional water were added to yield the consistency appropriate for application by brushing. The composition was applied to curing cement and, after curing, the composition was easily removed.

EXAMPLE 16b

This cellulosic mass was prepared as in Example 16a except that talc flakes of approximately 1 to 5 mm size were used in place of mica. This composition was about as easy to remove from substrate as that of Example 16a.

EXAMPLE 17a

Solar energy absorbing compositions (that can be left in place after moist cement curing was complete) were prepared using two coats of cellulosic material. The first coat was the material of Example 14 and the second outer coat was the material of Example 16a with the addition of 2% by weight carbon black.

EXAMPLE 17b

Compositions that reflect solar energy can be prepared as in Example 17a except that, instead of carbon black, 4% titanium dioxide was added to the cellulosic mass of the outer coating.

EXAMPLE 18

Four separate but similar three coat insulative compositions have been found to maintain, over a two week span, satisfactory curing conditions for the underlying cement in severe conditions of sunshine and wind. A representative three coat insulative composition had the material of Example 14 as the inner coat; the material of Example 14 further containing, as an insulative material, 20% by weight exfoliated vermiculite as a second coat; and the material of Example 14 as a top coat.

The third coat can be substituted with a dispersion of a "leafing" aluminum flake pigment and a synthetic resin such as an alkyd resin or a urethane resin applied in a volatile carrier solvent. These aluminum topcoat compositions give by far the best moisture retention among the exemplified compositions. Other resins may replace the exemplified resins, for instance, Cellulose acetate (Eastman Chem., Kingsport, Tenn.) and Polyvinyl acetate (Reichhold, White Plains, N.Y.).

EXAMPLE 19

The insulative material of the second coat of Example 18 was substituted with a cellulosic mass wherein ground, water-resistant, resin treated paper or cardboard was used as the source of cellulose fibers. These coated cellulose materials were useful mainly for second and third coatings of insulative compositions. Since the cellulose of this variant absorbs less water, the amount of water per g cellulose fibers correspondingly decreases to a range of 4 g to 20 g. The components of one such system are shown below:

| Component | Amount |
| --- | --- |
| Polyethylene coated cardboard[1] (10% polyethylene) ground to pass through a 30 mesh screen (approximately 550 microns) | 100.0 g |
| Carboxymethylcellulose | 5.0 g |
| Polyvinyl acetate emulsion (30% solids) (Reichhold, NY) | 25.0 g |
| Water | 150.0 g |

[1] Available from waste milk cartons and juice cartons. Scraps are available in bulk quantities from Kraft Paper, Atlanta, Georgia.

The components were mixed to obtain a homogeneous mixture. Approximately 250 g of additional water were added to obtain a mixture appropriate for application by brushing. This cellulosic mass can be used as a second coat in a two or a three coat composition. Equally satisfactory results are obtained if the polymer coating on the cardboard or paper was polypropylene or polyvinylacetate. The polymer coating used in this embodiment can also be cellulose acetate, ethyl cellulose, urea-formaldehyde resin, etc.

EXAMPLE 20

Preparation of Cellulose Fibers for Coating Vegetation

The fibers were prepared from old newsprint (ONP), ground in a hammer mill (Model D-G Fitz Mill, from Fitzpatrick Co., Elhurst, Ill.) to an average of 2 mm fiber length. The ONP was pre-moistened with about 15% water based on the weight of the ONP. Some of this water was lost during grinding due to evaporation. The ground fibers contained 10% water.

EXAMPLE 21

The fibers were prepared from polyethylene coated cardboard, ground in a hammer mill to an average fiber length of 3 mm. (Available from waste milk cartons and juice cartons. Scraps are available in bulk quantities from Kraft paper, Atlanta, Ga.) The cardboard used was coated with 10% polyethylene by weight of the cardboard. The ground material had a fluffy, wool-like texture and absorbed water slowly. The water-wet ground fibers do not mat to "papier mache" as do wetted fibers from polyethylene-free cardboard.

EXAMPLE 22

| The fibers of Example 20 | 1,000 g |
| --- | --- |
| Carboxymethyl cellulose, 75% CMC | 50 g |
| Sodium lauryl sulphate | 10 g |

The above components can be dry-mixed to obtain a homogeneous composition. The composition can be applied to plants and trees by means of a blow tube which has one to four water jets mounted at the exit port. The water jets are regulated to spray a fine mist of water onto the fiber mixture exiting from the blow tube. The presence of CMC in the fiber composition makes the composition very adhesive when wet. The moist fiber composition is used to protect the trunk, leaves and fruit of a number of trees. If the trees are in bloom they are further protected by adding a foaming surfactant to the water issuing from the jets at the exit of the tube.

The foam generated by the surfactant holds the fibers on top of the blossoms. The foam and fibers are removed with a gentle water spray after the frost danger has passed or may be allowed to remain on the blossoms to be washed off by rain.

EXAMPLE 23

| The fibers of Example 22 | 1,000 g |
| --- | --- |
| Polyvinyl alcohol (PVA) | 10 g |

Dry mix the fibers with the PVA. Use a 1% aqueous solution of PVA to wet the fibers leaving the pneumatic tube. The PVA will enable the fibers to adhere to tree trunks, branches and fruit. If the trees are in blossom the PVA is replaced in the water spray by the foaming surfactant mentioned in Example 22 (again using 10 g surfactant/1000 g fiber). The foaming agent protects the blossoms from mechanical damage.

EXAMPLE 24

Orange trees in full bloom were spray-coated with the fiber composition of Example 21. The blossoms were sprayed with the fiber composition using an Aerosol 18 solution for the hydrating spray (as in Example 23). This composition protected the blossoms during a 4 hour frost when the temperature dropped to 23°-25° F. (wind about 4-6 m.p.h.). The tree trunks were first sprayed with the moistening water solution containing 5% PVA to provide an adhesive layer for the fibers. The fiber composition was applied on the tree trunks using 15% aqueous solution of PVA in the hydrating spray. The tree trunks were given a 3 cm-thick fiber coating of which about 85% was airspace. The coating had the appearance and the feel of a fur coat. A coat like this protected orange trees for two days of cold weather (including time before and after the 23°-25° frost) when untreated trees in the same grove died.

EXAMPLE 25

Peach trees in bloom were coated with the blow tube technique in which the aqueous wetting spray contained 1% PVA and also 1% Aerosol 18. The spray solution to fiber ratio was kept about 15:85 which provided adequate foaming and adhesion to the blossoms. The fiber coating was removed with a gentle water spray.

EXAMPLE 26

The pneumatic tube technique performs well when coating low trees or shrubs, it is difficult and cumbersome to use the technique on tall trees with extensive foliage. The above difficulties were overcome and the technique was made suitable to coat whole groves of trees by using a modified Reinco Power Mulcher to apply the fiber composition. The Power Mulcher was modified by extending the ejection "boom" by about ten feet (or more, if necessary). This modification enabled the Power Mulcher to throw foamy fiber compositions to the tops of the trees. In addition to Reinco, Power Mulcher, similar equipment that is suitable for use in the present invention is made by Finn Corporation (Fairfield, Ohio) and others.

Since there is usually only a short time between a frost warning and the arrival of frost, it is important to protect the blossoms first by applying the fiber composition to the crowns of the trees with power mulcher type equipment. The fiber composition may also be applied to the tree trunks. If a severe frost or freeze is anticipated, it is especially advisable to apply the composition to the tree trunks.

Other adhesives in addition to CMC and PVA which are useful in the present invention include extracts of seaweed (e.g. Carrageenan from *Chondrus chrispus*).

For firefighting and cement curing applications, anionic or non-ionic surfactants can be added to the hydrated fibrous mass to increase the wetting properties of the mass. Suitable surfactants for use in the invention include glyceryl mono-oleate, sodium lauryl sulfate, and lignin sulfonate, among others. A preferred surfactant is sodium lauryl sulfate added in an amount from about 0.1 to 0.6% by weight of the dispersion. Higher proportions of surfactants such as sodium lauryl sulfate are undesirable because incorporation of air and foaming of the fiber dispersion will occur. Such foaming will reduce the weight to volume ratio of the hydrated fibrous mass reducing its overall effectiveness.

Also for firefighting, additives can be introduced to either the hydrated fibrous mass or the dry fibrous mass to increase the viscosity and therefore the cohesion and clinging properties of either fibrous mass. The following additives are preferred for use with the fibrous mass of the present invention: methylcellulose added at 1.0 to 4.0% by weight of the dispersion; carboxymethylcellulose added at between 1.0 to 4.0% by weight of the dispersion; and sodium silicate added at 3.0 to 15% by weight of the dispersion; and sodium alginate added at 1.0 to 10% by weight of the dispersion. These viscosity enhancers are preferably dissolved in water (with mixing) before the addition of the cellulosic fiber source.

Various bio-mass sources of cellulosic fibers can be used to provide the fibrous mass used in any embodiment of the present invention. Such materials include corn cobs, corn stalks, straw, oat hulls or other grain straw, cane, sugar cane bagasse, dry leaves and cardboard.

For firefighting and cement curing applications, Urea (at 10-80% by weight of the dispersion) or sodium hydroxide (at 5-15% by weight of the dispersion) can provide the required degree of swelling. Depending on the cellulosic fiber source, fiber swelling should be between about 50-200%.

In addition to serving as a useful firefighting aid, the fibrous mass of the present invention can be used in agricultural applications. The mass may be spread on to the soil surface at a thickness necessary to supply moisture to the soil and to release water over a period of time while keeping it near the surface. If the material is to be applied to a dry, water-repellent surface, the addition of a surfactant to the mass will overcome the initial repellency of the soil surface. Suitable surfactants for use in the invention include glyceryl mono-oleate, sodium lauryl sulfate and lignin sulfonate, among others.

The fibrous mass of the present invention can also be used as a carrier for fertilizers, herbicides or pesticides. The aerial application of herbicides and pesticides can be more efficient by reducing loss through wind drift by incorporating the pesticides or herbicides into the mass of the present invention and then applying the mass to the desired location. The pesticides which can be employed as adjuvants to the fibrous mass include any water soluble or water dispersible herbicide or insecticide such as diazinone and ammonium sulfonate, among others.

As described in the above examples, the fibrous mass of the present invention can also be used to control the rate of cure of fresh cement or concrete by applying the mass to the surface of the fresh cement or concrete at a desired thickness to form a hydrated mat. After the cement or concrete has cured properly, the fibrous residue of the hydrated mat can be easily removed by sweeping or vacuuming, or with a stream of water applied with sufficient force to remove the fibrous residue from the surface of the cement or concrete.

If desired, the individual cellulosic fibers can be granulated or encapsulated prior to mixing with water. Granulation or encapsulation of the fibers makes it easier to mix the fibers with water, and also makes it easier to store and transport the fibers. The fibers may be granulated by, for example, rolling with an adhesive, such as carboxymethyl cellulose, in a Mix Muller mixer. The adhesive is sprayed during the rolling step. The fibers eventually form granules held together by the adhesive. The fibers are ideally mixed with desired adjuvants, such as fire retardants or surfactants, prior to granulation. Encapsulation can be carried out by any number of known techniques.

It will be apparent to a person of ordinary skill in the art having the benefit of the present disclosure that many additions or omissions to the above-described coating method and coating composition are within ordinary skill in the art. Such additions or omissions are within the scope of the present invention as claimed below.

I claim:

1. A method of protecting plants and attendant fruit or blossoms comprising
   coating said plants with a composition comprising cellulose fibers, an adhesive and a foaming surfactant, said coating resulting in the adherence of said composition to the leaves, blossoms or blossom-forming bud structures of said plants.

2. The method of claim 1, wherein said cellulose fibers are obtained by grinding up a cellulose fiber source, said source selected from the group consisting of old newspapers, cornstalks, cardboard, polyethylene coated cardboard, wood pulp, straw, leaves and mixtures thereof.

3. The method of claim 2, wherein said fibers have a average fiber length between about 1 mm and about 10 mm.

4. The method of claim 1, wherein said adhesive is selected from the group consisting of carboxymethyl cellulose, polyvinylalcohol, seaweed extract and Carrageenan.

5. The method of claim 2, wherein said polyethylene-coated cardboard contains between about 5% and about 20% by weight polyethylene.

6. The method of claim 1, wherein said foaming surfactant is selected from the group defined by Formulas I and II:

-continued $$\underset{M^+ \; ^-O_3S-CH-CO_2-R_4}{CH_2-CO_2-R_3} \quad \text{II}$$

where M is sodium or potassium, where $R_1$ is H, carboxy($C_{2-4}$)alkyl or its sodium or potassium salts, or dicarboxy($C_{2-4}$)alkyl or its sodium or potassium salts, where $R_2$ is ($C_{14-22}$)alkyl, and where $R_3$ and $R_4$ are $C_{(8-12)}$alkyl.

7. The method of claim 6, wherein the surfactant is selected from the group consisting of Aerosol 18, Aerosol 22, Aerosol OT and mixtures thereof.

8. A cellulose fiber composition comprising cellulose fibers having a length of between about 1 mm and about 10 mm, an adhesive, and a surfactant selected from the group defined by Formulas I and II:

$$\underset{M^+ \; ^-O_3S-CH-CO_2-NR_1R_2}{CH_2-CO_2^- \; M^+} \quad \text{I}$$

$$\underset{M^+ \; ^-O_3S-CH-CO_2-R_4}{CH_2-CO_2-R_3} \quad \text{II}$$

where M is sodium or potassium, where $R_1$ is H, carboxy($C_{2-4}$)alkyl or its sodium or potassium salts, or dicarboxy($C_{2-4}$)alkyl or its sodium or potassium salts, where $R_2$ is ($C_{14-22}$)alkyl, and where $R_3$ and $R_4$ are $C_{(8-12)}$alkyl.

9. The cellulose fiber composition of claim 9, wherein said adhesive is selected from the group consisting of carboxymethyl cellulose, polyvinylalcohol, seaweed extract and Carrageenan.

10. The method of claim 10, wherein the surfactant is selected from the group consisting of Aerosol 18, Aerosol 22, Aerosol OT and mixtures thereof.

11. A method of protecting plants and attendant fruit or blossoms by coating said plants with a foaming composition comprising cellulose fibers, an adhesive, water and a foaming surfactant, said method comprising:
providing a coating composition comprising said fibers and;
providing a container containing said composition;
providing a means of ejecting said coating composition from said container;
providing an aqueous liquid;
providing an adhesive added to at least one of said coating composition and said aqueous liquid;
providing a means of spraying fibers ejected from said ejecting means with said aqueous liquid;
ejecting said coating composition toward said plants; concomitantly spraying said ejected coating composition with an aqueous liquid; and
thereby coating a portion of said plants with a foamy cellulosic composition.

12. The method of protecting plants and attendant fruit or blossoms by coating said plants with a cellulosic composition of claim 11, further comprising a surfactant added to at least one of said coating composition and said aqueous liquid and wherein said coated portion of said plants is coated with a foamy cellulosic composition.

13. The method of protecting plants and attendant fruit or blossoms by coating said plants with a cellulosic composition of claim 12, wherein said surfactant is added to said aqueous liquid.

14. The method of protecting plants and attendant fruit or blossoms by coating said plants with a cellulosic composition of claim 12, wherein said surfactant is added to said coating composition.

15. The composition of protecting plants and attendant fruit or blossoms by coating said plants with a cellulosic composition of claim 12, wherein said surfactant comprises a compound selected from the group defined by Formulas I and II:

$$\underset{M^+ \; ^-O_3S-CH-CO_2-NR_1R_2}{CH_2-CO_2^- M^+} \quad \text{I}$$

$$\underset{M^+ \; ^-O_3S-CH-CO_2-R_4}{CH_2-CO_2-R_3} \quad \text{II}$$

where M is sodium or potassium, where $R_1$ is H, carboxy($C_{2-4}$)alkyl or its sodium or potassium salts, or dicarboxy($C_{2-4}$)alkyl or its sodium or potassium salts, where $R_2$ is ($C_{14-22}$)alkyl, and where $R_3$ and $R_4$ are $C_{(8-12)}$alkyl.

16. The method of protecting plants and attendant fruit or blossoms by coating said plants with a cellulosic composition of claim 14, wherein said surfactant is selected from the group consisting of Aerosol 18, Aerosol 22, Aerosol OT and mixtures thereof.

17. The method of protecting plants and attendant fruit or blossoms by coating said plants with a cellulosic composition of claim 12, wherein said cellulosic fibers comprise cardboard coated with between about 5% and about 20% by weight polyethylene.

18. The method of protecting plants and attendant fruit or blossoms by coating said plants with a cellulosic composition of claim 11, wherein said adhesive is selected from the group consisting of carboxymethyl cellulose, polyvinylalcohol, seaweed extract and Carrageenan.

* * * * *